US009814737B2

(12) United States Patent
Huckfeldt et al.

(10) Patent No.: US 9,814,737 B2
(45) Date of Patent: Nov. 14, 2017

(54) COMPOSITION FOR SKIN SANITIZATION AND PROTECTION AND METHOD OF ITS USE

(75) Inventors: Roger Huckfeldt, Nixa, MO (US); Phillip Finley, Springfield, MO (US)

(73) Assignee: Mercy Medical Research Institute, Springfield, MO (US)

( * ) Notice: Subject to any disclaimer, the term of this patent is extended or adjusted under 35 U.S.C. 154(b) by 6 days.

(21) Appl. No.: 13/095,708

(22) Filed: Apr. 27, 2011

(65) Prior Publication Data

US 2011/0262558 A1 Oct. 27, 2011

Related U.S. Application Data

(60) Provisional application No. 61/328,360, filed on Apr. 27, 2010.

(51) Int. Cl.
| | | |
|---|---|---|
| *A61K 31/60* | (2006.01) | |
| *A61K 31/695* | (2006.01) | |
| *A61K 31/235* | (2006.01) | |
| *A61P 17/00* | (2006.01) | |
| *A61K 36/752* | (2006.01) | |
| *A61K 31/194* | (2006.01) | |
| *A61K 8/19* | (2006.01) | |
| *A61K 8/365* | (2006.01) | |
| *A61K 8/368* | (2006.01) | |
| *A61K 8/44* | (2006.01) | |
| *A61K 8/60* | (2006.01) | |
| *A61K 31/14* | (2006.01) | |
| *A61K 31/191* | (2006.01) | |
| *A61K 31/4166* | (2006.01) | |
| *A61K 45/06* | (2006.01) | |
| *A61Q 17/00* | (2006.01) | |
| *A61Q 17/04* | (2006.01) | |
| *A61Q 19/10* | (2006.01) | |
| *A61K 33/38* | (2006.01) | |

(52) U.S. Cl.
CPC .............. *A61K 31/695* (2013.01); *A61K 8/19* (2013.01); *A61K 8/365* (2013.01); *A61K 8/368* (2013.01); *A61K 8/44* (2013.01); *A61K 8/602* (2013.01); *A61K 31/14* (2013.01); *A61K 31/191* (2013.01); *A61K 31/194* (2013.01); *A61K 31/235* (2013.01); *A61K 31/4166* (2013.01); *A61K 31/60* (2013.01); *A61K 33/38* (2013.01); *A61K 36/752* (2013.01); *A61K 45/06* (2013.01); *A61Q 17/005* (2013.01); *A61Q 17/04* (2013.01); *A61Q 19/10* (2013.01)

(58) Field of Classification Search
CPC .................................................. A61K 36/572
See application file for complete search history.

(56) References Cited

U.S. PATENT DOCUMENTS

| | | | | |
|---|---|---|---|---|
| 4,438,102 | A | | 3/1984 | Ganci |
| 4,604,281 | A | * | 8/1986 | Deckner et al. ............... 424/59 |
| 4,900,721 | A | | 2/1990 | Bansemier et al. |
| 5,139,788 | A | | 8/1992 | Schmidt |
| 5,605,894 | A | * | 2/1997 | Blank et al. .................. 514/159 |
| 6,358,516 | B1 | * | 3/2002 | Harod ........................... 424/401 |
| 6,488,948 | B1 | * | 12/2002 | Danieli ................. A61K 31/14 |
| | | | | 424/402 |
| 6,727,210 | B1 | | 4/2004 | Perdew, Jr. |
| 6,805,874 | B1 | * | 10/2004 | Lutz et al. .................... 424/401 |
| 2002/0009423 | A1 | | 1/2002 | Murad |
| 2004/0116551 | A1 | * | 6/2004 | Terry ............................ 523/122 |
| 2005/0053563 | A1 | * | 3/2005 | Manissier et al. .......... 424/70.13 |
| 2005/0152863 | A1 | * | 7/2005 | Brautigam et al. .......... 424/70.1 |
| 2005/0255132 | A1 | * | 11/2005 | Rabiner ........................ 424/401 |
| 2006/0051429 | A1 | | 3/2006 | Murad |
| 2006/0182770 | A1 | * | 8/2006 | Tanojo et al. ................. 424/400 |
| 2006/0204468 | A1 | * | 9/2006 | Allef et al. ................ 424/70.13 |
| 2007/0098647 | A1 | * | 5/2007 | Neubourg ....................... 424/47 |
| 2007/0122364 | A1 | * | 5/2007 | Kelly et al. ..................... 424/59 |
| 2009/0123397 | A1 | * | 5/2009 | Seal et al. ........................ 424/59 |
| 2011/0182958 | A1 | * | 7/2011 | Omidbakhsh ................ 424/405 |

FOREIGN PATENT DOCUMENTS

| | | | |
|---|---|---|---|
| JP | 2006299163 | A | 11/2006 |
| JP | 2008156335 | A | 7/2008 |
| WO | 9740816 | A1 | 11/1997 |

OTHER PUBLICATIONS

DOW (product description for VERSENE 100) 2007 http://web.archive.org/web/20070401074729/http://www.dow.com/productsafety/finder/edta.htm.*
Conner 2004. http://web.archive.org/web/20070206183533/http://www.compassionateacupuncture.com/Immune%20System%20Enhancement.htm.*
Heal Yourself At Home. Grapefruitseed Extract Information about Citricidal. Retrieved online May 2016.*
PCT Patent Application PCT/US2011/034196 International Search Report & Written Opinion dated Apr. 27, 2011, 10 pages.
European Patent Application 11777978.5 Search Report dated Sep. 16, 2013, 11 pages.
"Vitamin E Treatment Cleansing Foam", Mintel GNPD, Jun. 1, 2009 (Jun. 1, 2009), pp. 1-3, XP055077446, Retrieved from the Internet: URL: http://www.gnpd.com/sinatra/gnpd/search_results&search_id=1NS72q6uZu/item_id=1109364 [retrieved on Sep. 3, 2013].

(Continued)

*Primary Examiner* — Adam C Milligan
*Assistant Examiner* — Sarah Alawadi
(74) *Attorney, Agent, or Firm* — Polsinelli PC

(57) ABSTRACT

An improved composition for skin cleansing and protection is disclosed. The composition contains an effective amount of at least one alpha-hydroxyl acid or a pharmaceutically acceptable salt thereof, at least one base, one surfactant and one skin protectant. Various additives and excipients may be included in the formulation. The improved composition disclosed herein achieves a higher bacteria killing rate and shows longer action duration. The disclosed composition is capable of penetrating deep into the skin which allows for delivery of more anti-microbials to sites that are at a higher risk of being infected. Various modifications of the improved composition are also disclosed.

1 Claim, No Drawings

(56) References Cited

OTHER PUBLICATIONS

"Soothing Moisturizing Antibacterial Handwash. Tesco", Mintel GNPD, Mar. 1, 2010 (Mar. 1, 2010), pp. 1-2, XP055077443, Retrieved from the Internet: URL: http://www.gnpd.com/sinatra/gnpd/search_results&search_id=gem2uqEpDJ/&p_page_number=8&item_id=1289089 [retrieved on Sep. 3, 2013].

"Sunflower Hand Soap", Mintel GNPD, Jan. 1, 2010 (Jan. 1, 2010), pp. 1-2, XP055077440, Retrieved from the Internet: URL: http://www.gnpd.com/sinatra/gnpd/search results&search id=yY26yNrwlt/&p_page_number=1&p_page_size=30&item_id=1261031 [retrieved on Sep. 3, 2013].

"Deo-Shower Gel Nivea for Men", Mintel GNPD, Mar. 1, 2010 (Mar. 1, 2010), pp. 1-2, XP055077441, Retrieved from the Internet: URL:http://www.gnpd.com/sinatra/gnpd/searchresults&searchid=zxZCa8Kapn/&itemid=1283484 [retrieved on Sep. 3, 2013].

"Acne Scar Reduction System. Dermajuv", Mintel GN PO, Feb. 1, 2010 (Feb. 1, 2010), pp. 1-8, XP055077577, Retrieved from the Internet:URL:http://www.gnpd.com/sinatra/gnpd/searchresults&searchid=arUKhu5Myr/&p_page_number=4&item_id=1281939 [retrieved on Sep. 4, 2013].

"Cream Shower. Lotto", Mintel GNPD, Oct. 1, 2009 (Oct. 1, 2009), pp. 1-2, XP055077645, Retrieved from the Internet: URL:http://www.gnpd.com/sinatra/gnpd/search-results&search-id=fYmc6PMKOC/&item-id=1184304 [retrieved on Sep. 4, 2013].

\* cited by examiner

COMPOSITION FOR SKIN SANITIZATION AND PROTECTION AND METHOD OF ITS USE

RELATED APPLICATIONS

This application claims priority to U.S. Patent application 61/328,360 filed Apr. 27, 2010, the entire content of which is hereby incorporated by reference into this application.

BACKGROUND

1. Field of the Invention

This disclosure relates to skin sanitizing compositions and methods for skin cleansing and for prevention and treatment of skin infection.

2. Description of Related Art

Human skin is a composite material made up of two primary sections, the epidermis and the dermis. The epidermis lies on top of the dermis. The top-most layer of the epidermis is called the stratum corneum. The stratum corneum is the stiffest layer of the skin, and is also the layer of the skin that is most affected by the outside environment. Underneath the stratum corneum is the internal layer of the epidermis. Below the epidermis, the top-most layer of the dermis is called the papillary dermis. The papillary dermis is made of relatively loose connective tissues that define the micro-relief of the skin. Beneath the papillary dermis lies the reticular dermis, which is made of tight, connective tissues. At the bottom of the dermis lies the subcutaneous layer.

The major functions of the skin include protection, excretion, secretion, absorption, thermoregulation, pigmentogenesis, accumulation, sensory perception, and regulation of immunological processes. Because of its unique position as the outermost barrier of the human body, human skin is vulnerable to infection by microorganisms in the environment. The protective role of the skin can be compromised when the skin itself is infected or colonized by microorganisms.

Many compositions have been used for skin cleansing, and for treatment or prevention of skin infection. For instance, U.S. Pat. No. 4,438,102 discloses compositions containing gelatin, hydrogen peroxide, ammonium hydroxide, thioglycolic acid, and a lower alkanol to promote the growth of dermal and epidermal tissues.

U.S. Pat. No. 4,900,721 discloses an aqueous disinfectant based on alcohol and hydrogen peroxide. The disinfectant contains one or more $C_2$-$C_8$ alcohols, hydrogen peroxide or a hydrogen peroxide forming compound, one or more carboxylic acids, one or more microbicidally active nitrogen-containing organic compounds, one or more microbicidally active phenolic compounds for disinfection of the skin and mucous membrane.

U.S. Pat. No. 5,139,788 discloses an antimicrobial surface sanitizing composition having a diluent and an antimicrobially effective amount of alpha-hydroxyacid substituted mono- or di-carboxylic acid and an antimicrobially effective amount of hydrogen peroxide, such that the composition leaves a non-contaminating residue after contact with surfaces to be disinfected.

U.S. Pat. No. 5,693,318 discloses phosphate esters for the improvement of water solubility of salicylic acid and peroxide compounds in an aqueous cleanser.

U.S. Pat. No. 6,358,516 discloses a skin care system that cleanses, and therapeutically conditions the skin in a one-step application. The system employs cloths that are impregnated with a treatment composition. The treatment composition of the '516 patent contains a plurality of ingredients such as surfactants, anti-inflammatory agents, non-foaming agents, cell-growth-promoting agents, immune system-enhancing agents, antimicrobial agents, absorption facilitating agents, humectants and emollients, free radical-scavenging agents, healing promoting agents, preservatives and fragrances.

Despite all these efforts, none of the skin cleansing and protecting compositions provide deep penetration into the skin so that the therapeutic agents contained in the composition may reach deep into the areas that are most likely to be infected or colonized by pathogenic microorganisms. Moreover, due to the lack of deep penetration, currently available compositions do not provide long-term protection from infections such as folliculitis, dermatitis, psoriasis, rosacea, and the like.

SUMMARY

The instrumentalities disclosed herein advance the art and overcome the problems outlined above by providing compositions and methods for cleansing and protecting the skin of a subject, such as a mammal, and most preferably a human. In one embodiment, a composition is disclosed which contains at least four components: at least one acid or a pharmaceutically acceptable salt thereof, at least one base, at least one surfactant, and at least one skin protectant. In one aspect, one or more of the at least four components may be the same. In another aspect, the at least four components are chemically different from one another. The composition preferably has a pH of between 5 and 7, or more preferably, between 6 and 6.7, and even more preferably, between 6.3 and 6.7.

In one embodiment, the composition suitable for cleansing and/or protecting the skin may contain at least four different components: (a) one alpha-hydroxyl acid or a pharmaceutically acceptable salt thereof, (b) at least one base, (c) at least one surfactant, and (d) at least one skin protectant, wherein the ingredients of (a)-(d) are chemically different from one another. The concentration of these components are preferably 0.1-2% for (a), 0.2-2% for (b), 2-16% for (c), and 0.2-3% for (d) by weight of the composition. The composition may have a pH between 5 and 7, more preferably, between 6 and 6.7, and even more preferably, between 6.3 and 6.7.

A number of different solvents may be used as the primary solvent for the composition(s) disclosed herein. In one embodiment, water is used as the solvent. In another embodiment, the composition may contain approximately 70-90%, or about 80-85%, of water by weight of the composition.

Although a beta-hydroxyl acid may be used in the composition, the preferred acid suitable for the disclosed composition(s) is an alpha-hydroxyl acid. In one embodiment, the acid may be glycolic acid, lactic acid, citric acid, salicylic acid, or tannic acid. In another embodiment, the acid is glycolic acid at a concentration from about 0.1-2% (w/w) in the composition. The at least one acid or its salt thereof is preferably present in the instant composition in an amount that is effective to exfoliate at least a portion of the skin when said composition is applied to the skin.

Suitable surfactants may be selected from a number of commonly used surfactants that are capable of cleansing the surface areas as well as high risk areas of the skin without inactivating the antimicrobial agents. High risk areas in the skin include but are not limited to peri-hair follicles and deep layers of epidermis. Preferably, the surfactants do not cause significant skin irritation. Thus, the composition allows single stage cleansing and does not require extra washing or rinsing between the cleansing step and the treatment step. In one preferred embodiment, the at least one surfactant to be used in the composition is a zwitterionic surfactant, such as betaine.

The composition may also contain at least one base to provide a pH adjusting and buffering capability. Potassium hydroxide is the preferred base but a number of other bases may be used. The concentration of the potassium hydroxide is preferably about 0.2-2% by weight of the composition.

The at least one skin protectant may be allantoin, or dimethicone and combination thereof.

In another embodiment, the disclosed composition may further contain at least one member from each of the following functional categories of additives: a stabilizer, a preservative, a moisturizer, an immune system-enhancing agent, an anti-microbial agent, an anti-inflammatory agent, an anti-foaming agent, a cell growth-promoting agent, a nutrient that helps nourish the cells of the skin, an absorption facilitating agent, a humectant, an emollient, a free radical-scavenging agent, a healing promoting agent, among others.

It is to be recognized that certain additives may perform more than one function. For instance, one agent may be both a stabilizer and a preservative. It is also to be understood that the at least one acid or salt thereof, the at least one base, the at least one surfactant, or the at least one skin protectant contained within the disclosed composition may also be capable of performing one or more of the functions listed above, namely, as a stabilizer, a preservative, a moisturizer, an immune system-enhancing agent, an anti-microbial agent, an anti-inflammatory agent, an anti-foaming agent, a cell growth-promoting agent, a nutrient that helps nourish the cells of the skin, an absorption facilitating agent, a humectant, an emollient, a free radical-scavenging agent, or a healing promoting agent.

In another embodiment, the composition may optionally contain at least one immune system-enhancing agent. The immune system-enhancing agent may interact with the immune system of the subject and may enhance the effectiveness of the immune system in fighting infections of the skin. Examples of such immune system-enhancing agent may include but are not limited to aloe vera, beta-glucan, colloidal silver, allantoin, or combination thereof.

In another embodiment, the composition may contain at least one anti-microbial agent. Examples of the anti-microbial agent may include but are not limited to colloidal silver, grapefruit seed extract, benzalkonium chloride, or combination thereof.

In another embodiment, the composition may contain at least one preservative to help stabilize the anti-microbials. Examples of the preservative may include but are not limited to lauryl glucoside, or phenonip. Phenonip is a commercially available preservative that is made up of methylparaben, butylparaben, ethylparaben, propylparaben, isobutylparaben, phenoxyethanol.

The composition may further contain at least one chelating agent to help protect the anti-microbials from being inactivated. Examples of the chelating agent may include but are not limited to versene 100 EDTA.

The composition may further contain one or more fragrances.

The concentration ranges of various components or additives for the disclosed composition are provided as a general guideline but not as a further limitation of the scope of this disclosure. For instance, aloe vera may be present at a concentration of about 3-15% by weight of the composition. Colloidal silver may be present at a concentration of about 0.1-2% by weight of the composition. Allantoin may be present at a concentration of about 0.3-2% by weight of the composition. Dimethicone may be present at a concentration of about 0.15-1% by weight of the composition. Lauryl glycoside may be present at a concentration of about 0.1-0.6% by weight of the composition. The chelating agent, such as versene 100 EDTA, may be present at a concentration of about 0.01-0.1% by weight of the composition. Benzalkonium chloride may be present at a concentration of about 0.005-0.13% by weight of the composition. Phenonip may be present at a concentration of about 0.3-2% by weight of the composition.

One objective of the present disclosure is to prevent microbial infection in the skin. Another objective is to eradicate or reduce the number of microorganisms that have infected the skin by delivery of anti-microbial agents to the sites of infections. Yet another objective is to improve the overall health of the skin by providing nutrients and/or other ingredients to the skin.

In one embodiment, the disclosed composition may be prepared in a liquid form and may be used to moisturize or saturate a cloth, a towel, a swab, or a tissue, which may be used to apply the composition onto a surface, such as the skin of an animal or a human. In another embodiment, the instant composition may be prepared as a product suitable for cleansing or protecting the hair, skin or fur of an animal.

In another embodiment, the composition may also be used alone or in combination with other active or inactive ingredients to form a product for cleansing a wound area.

In another embodiment, the disclosed composition may contain one or more natural ingredients. In one aspect, the composition may contain an amount of grapefruit seed extract, or grape seed extract.

Other excipients, additives and/or solvents may be added to the instant composition in order to manufacture a material/product suitable for skin cleansing and/or protection. Such materials/products may be in the form of a solution, a gel, a paste, a cream, a spray, a lotion, an emulsion, or an ointment. When applied to the skin, some components of the disclosed composition may penetrate the outer layer of the epidermis, thus allowing certain nutritional or pharmaceutical agents to reach areas that are in need of being treated by such agents. By way of example, areas that are in need of such treatment include peri-hair follicles and deep layers of epidermis which are usually unreachable by most skin sanitizing compositions.

DETAILED DESCRIPTION

The present disclosure relates to improved compositions and methods for sanitizing and protecting the skin. The improved compositions and modifications thereof show at least a one log, 1.5 log, 2 log, or 3 log reduction of bacteria as compared to cleansing and treatment by conventional soap and water, or by a conventional hand sanitizer containing the same anti-microbials. The improved compositions and modifications thereof also shows a longer duration of action.

The terms "agent," "ingredient," "component," and "constituent" may be used interchangeably in this disclosure.

The compositions of the present disclosure may contain one or more of the ingredients listed below or combination thereof. It is to be understood that additional ingredients may be included which may confer upon the disclosed compositions certain desirable properties. Examples of such desirable properties may include but are not limited to enhanced killing of pathogenic microorganisms, enhanced protection of beneficial microorganisms, increased stability of the composition, reduced irritation to the skin and so on.

(a) Acids. The acid ingredient may help various agents of the disclosed composition penetrate the skin and reach areas deep inside the skin that are at risk of being infected. In one embodiment, the disclosed composition contains at least one acid. Examples of the acid include but are not limited to an alpha-hydroxyl acid, a beta-hydroxyl acid and combination thereof. Preferably, the at least one acid is an alpha-hydroxyl acid, such as glycolic acid, lactic acid, citric acid, salicylic acid, tannic acid, and combination thereof. Glycolic acid may react with the upper layer of the epidermis and weaken the binding ability of the lipids that hold the outer layer (dead skin cells) together. This action, in turn, allows the active ingredients, such as anti-microbials, to reach below this upper layer to achieve their functions in areas that are at a high risk of being infected. Glycolic acid and other alpha hydroxyl acids are known to cause skin irritation. The amount of the alpha-hydroxyl acids in the present compositions is kept sufficiently low, and the pH of the composition is maintained at a stabilized pH of 6-7, or more preferably, at pH 6.3-6.7 in order to prevent skin irritation while achieving their normal functions of loosening the outer layer of the skin.

(b) Base. Different bases may be used for the composition. Potassium hydroxide is the preferred base. The base may provide to the compositions a pH buffering capability. The base also serves as a source of the hydroxyl groups which attack polar bonds in organic material, such as the fats or lipids on the skin. This action helps saponify esters and converts fats into soaps. This property is widely employed in soap manufacturing but has not been used in chemical skin sanitizers. The unique combination of antimicrobials and base in the present composition helps remove organic material or oils that are present at the skin level and thus allow the antimicrobials to stay active longer. Moreover, like other bases, the potassium hydroxide may force the hair cuticle open and may thus act as a hygroscopic agent to attract and force water (and therefore associated antimicrobials and skin protectants) into the hair shaft. The dosage of the base is controlled to allow such opening without damaging the viability or structure of the hair follicles.

(c) Cleansing agents, such as surfactants and/or soaps. These may include but are not limited to amphoteric/zwitterionic surfactants (i.e., surfactants having the capacity of behaving either as an acid or a base), cocamidopropyl betain, alkyl polyglucosides, lauryl glucoside, and combinations thereof.

While mild soaps may be used with the present compositions, surfactants are preferred. Surfactants lift soil off the skin by reducing the surface tension, whereas soaps remove protective emollients from the skin and can disturb the normal pH.

Zwitterionic surfactant may allow cleansing of surface areas and may also reach deep into high risk areas (peri-hair follicles, deep layers of epidermis) without inactivating the antimicrobial agents. The low skin irritation allows single stage cleansing without requiring extra intervening washes. Betaine such as Tego Betaine 810 Surfactant is the preferred cleansing agent.

(d) Skin protective agent (or skin protectant). One or more skin protectants may be included in the composition. Examples of skin protectant may include but are not limited to allantoin and dimethicone, both of which are FDA approved skin protectants.

(e) Agents that stimulate or promote cell growth. These may include but are not limited to aloe vera, allantoin (glyoxyldiureide; 5-ureidohydantoin), beta glucan, polyphenolic compounds and combinations thereof. These compounds may contain certain quaternary compounds derived from grapefruit or other bioflavonoids, along with inert ingredients such as glycerin. Growth-promoting agents may promote or stimulate new skin growth and help improve the overall health of the skin.

(f) Agents that enhance and/or stimulate the immune system of the subject to whom the compositions are to be applied. These may include but are not limited to aloe vera, beta glucan, colloidal silver, allantoin, and combinations thereof. When present in the composition in the preferred quantities, these agents may help enhance the host immune system and also help reduce the incidence of infections.

Colloidal silver is a naturally occurring antimicrobial, and may support the natural immune system by reducing its workload. Aloe vera is a recognized skin health agent and allantoin is an FDA recognized skin protectant.

(g) Anti-microbial agents. The skin harbors a wide variety of microorganisms, some of which are potentially harmful while others are beneficial. Ideally, this normal bacterial flora is not destroyed by cleansing. However, a cleanser that reduces the accumulation of bacteria, fungi, etc. present on the skin helps reduce the incidence of skin infections, especially in a hospital environment. Suitable anti-microbials may include agents that are effective against bacteria, viruses, yeasts or other fungi. For purpose of this disclosure, the anti-microbial can be fast-acting or slow-acting anti-microbial that is compatible with the skin.

Example of suitable anti-microbial agents include but are not limited to colloidal silver, benzalkonium and salts thereof, pycnogenol, grape seed extract, grapefruit seed extract, antibiotics, and combinations thereof, in effective amounts to kill infectious bacteria, viruses, yeasts, and fungi on and in the skin. Grapefruit seed extract is a naturally occurring antimicrobial agent that is especially effective against gram negative bacteria. Benzalkonium chloride is an FDA approved antimicrobial agent.

Some anti-microbial agents, such as colloidal silver, are compatible with normal flora, and are capable of penetrating into the dermis. Colloidal silver kills single-cell microorganisms such as bacteria by penetrating their cell walls. Therefore, these organisms cannot mutate into resistant strains as they do with many other antimicrobial agents. However, colloidal silver has limited potency and must preferably be supplemented with other antimicrobial agents in formulating a composition according to the invention. In addition, the colloidal silver is preferably formulated with particles that are small enough to penetrate the dermis, for examples, with particles that are approximately 0.005-0.02 microns; or more preferably, approximately 0.01-0.1 microns.

(h) Agents that, by their particle size and/or function, facilitate absorption into the second layer of the skin or dermis Such agents may include but are not limited to beta-glucan, aloe vera, colloidal silver, allantoin, and combinations thereof.

(i) Compatible humectants and emollients. Humectants and emollients in the composition may help re-moisturize the skin surface (i.e., the dermis) to prevent dryness, and may increase elasticity, reduce the incidence of skin tears, and supplement the activity of the sebaceous glands to reproduce oils without clogging the pores. Over-usage of humectants and/or emollients is a major cause of skin eruptions, inflammation, and acne, therefore, simply increasing the amounts of humectants and/or emulsifiers to provide a longer lasting protective barrier can actually cause skin problems. Therefore, the amounts of these ingredients should be controlled so as to minimize such undesirable effects. Examples of humectants and emollients may include but are not limited to aloe vera, allantoin, vitamin E (tocopherol), beta-glucan, cocamidopropyl betain, and combinations thereof.

(j) Agents that scavenge free radicals and help detoxify the skin. Examples of such scavenging agents may include but are not limited to beta-glucan, allantoin, vitamin E, pycnogenol, grape seed extract, and combinations thereof. Preferably, the disclosed composition contain a sufficient quantity of one or more of these agents in a form that is delivered deeper than the dead horny layer of the skin in use.

(k) Biocompatible preservatives. The preservatives suitable for the instant composition are compatible with the skin. Examples of such biocompatible preservatives include but are not limited to phenonip, methylparaben, propylparaben, ethylenediamine-tetraacetic acid (EDTA)-like agents, and combinations thereof. Phenonip is a commercially available preservative that is made up of methylparaben, butylparaben, ethylparaben, propylparaben, isobutylparaben and phenoxyethanol.

(l) Biocompatible fragrances. Fragrances that may be used in the composition of this disclosure include but are not limited to natural orange, lemon, lavender, and combinations thereof.

(m) Other beneficial agents, including but not limited to those containing vitamins and vitamin precursors (vitamin A, carotene, cryptoxanthin, retinol, 3-dehydroretinol, vitamin C (ascorbic acid), vitamin E (tocopherol), etc.), herbs (chamomile, lavender, ginseng, ginkgo, etc.), antioxidants, collagens, pH-balancing agents, and combinations thereof.

Not all ingredients (a)-(m) listed above have to be present in the compositions in order to achieve the desired effects of skin cleansing and/or protection. Each ingredient listed above may be effective either alone or synergistically with the other ingredients to achieve the desired results of skin cleansing and protection. By way of example, some of the above-listed ingredients are most effective when present in the amounts listed in Table 1.

Moreover, although the above-described ingredients have known beneficial effects, the mere presence of these ingredients in a formulation does not automatically result in a product that can help achieve the desired skin cleansing and protection effects. Many of the ingredients interact with each other and show synergistic effects when they are present in the same composition at suitable concentration ranges. For example, allantoin is nontoxic, nonirritating, and nonallergenic, and is known to help in skin healing when present in concentration of 0.2% or more. Allantoin is also an FDA-recognized skin protectant at concentration of 0.5%. However, allantoin tends to precipitate easily out of solution when present at concentrations exceeding 1%, and may have to be supported by other similar agents when formulating a composition according to the present disclosure.

TABLE 1

Advanced Hand Sanitizer Composition

| Ingredient | Suitable Conc. Range (w/w) |
| --- | --- |
| Purified water | 70-90% |
| Betaine* | 2-16% |
| Lauryl Glucoside | 0.1-0.6% |
| Versene 100 EDTA | 0.01-0.1% |
| Colloidal Silver | 0.1-2% |
| Aloe 10× concentrate | 3-15% |
| Benzalkonium chloride | 0.005-0.13% |
| Glycolic acid | 0.10-2% |
| Phenonip | 0.3-2% |
| Allantoin | 0.3-2% |
| Dimethicone | 0.15-1% |
| Potassium hydroxide | 0.2-2% |

*One example of betaine is Tego Betaine 810

Selected ingredients of those listed above in Table 1 (or others that provide similar functions) may be combined, preferably in an aqueous solution, to provide a therapeutic skin cleanser or skin protector according to the present disclosure. In one aspect, the ingredients used in the composition may be selected to be compatible with each other and with human skin even after exposure to temperatures in the range of 0-140 F, and/or sterilization by gamma or E-beam radiation.

The pH of the composition is preferably close to that of human skin, namely, approximately 5-7. However, compositions with a pH outside this range may also be useful. The composition is naturally pH-balanced when formulated with selected ingredients as described below. However, pH-balancing agents may be added if desired.

A composition according to the present disclosure contains at least one ingredient selected from each of groups (a)-(d). In one embodiment, the composition contains at least one ingredient selected from at least one of the groups (e)-(m) in an aqueous solution. In another embodiment, the composition includes at least 6 ingredients in addition to water: at least one ingredient from each of groups (a)-(d), ant at least two different ingredients from one of groups (e)-(m). In another embodiment, the composition contains all ingredients listed in Table 1. In another embodiment, the composition according to the present disclosure may contain the following ingredients: water, betaine, Colloidal Silver, Benzalkonium Chloride or other antimicrobials, Glycolic acid or other alpha hydroxy acids, Allantoin, Dimethicone, and Potassium hydroxide.

It is to be noted that, as used in this disclosure, the singular forms "a," "an," and "the" include plural referents unless the context clearly dictates otherwise. Thus, for example, reference to "a composition" includes reference to two or more of such compositions.

The disclosed compositions may be prepared and/or distributed in a concentrated form or a diluted form. A concentrate may be dissolved or dispersed in a solvent to form a reconstituted solution, typically referred as a "use dilution."

EXAMPLES

The following examples illustrate the present disclosure. These examples are provided for purposes of illustration only and are not intended to be limiting. The chemicals and other ingredients are presented as typical components or reactants, and various modifications may be derived in view of the foregoing disclosure within the scope of the invention.

Example 1

Preparation of an Advanced Hand Sanitizer Composition

An advanced sanitizer composition (also known as "Theraworx Exp") was prepared according to the formulations described in Table 2. v/v denotes percentage by volume when the individual ingredient is in a liquid form, and w/v denotes percentage by weight when the individual ingredient is in a solid (powder or granule) form.

TABLE 2

Advanced Hand Sanitizer Composition "Theraworx Exp" (Formula One)

| Ingredient | Concentration |
|---|---|
| Purified water | 815 ml/liter |
| Tego Betaine 810 | 2% v/v |
| Lauryl Glucoside | 0% |
| Versene 100 EDTA | 0.02% v/v |
| Colloidal Silver | 0.3% v/v |
| Aloe 10x concentrate | 5% v/v |
| Benzalkonium chloride | 0.13% v/v |
| Glycolic acid | 0.35% v/v |
| Phenonip | 0.5% v/v |
| Allantoin | 0.6% w/v |
| Dimethicone | 0.2% v/v |
| Potassium hydroxide | 0.406% w/v |

Example 2

The Advanced Hand Sanitizer Composition Shows High Bacteria Kill Rate

The composition prepared in Example 1 was tested for its capability to kill bacteria under established contact time. More specifically, the composition was caused to be in contact with four different bacterial species, MRSA, *Acinetobacter baumannii, E. coli* and *Serratia marcesans* for different periods of time including 15 seconds, 30 seconds or 60 seconds, and the percentages of each bacterial species that have been killed were determined and compared. Under established contact time, the kill rates for all tested bacteria are at least 99.99%.

Example 3

Variation of the Concentration of Different Ingredients

To test the effectiveness of the advanced hand sanitizer composition when different ingredients are present at different concentrations, nine different compositions, Formulae 2-10 were prepared as described below. Bacteria kill rate of these nine different compositions were tested according to the protocol described in Example 2. Formulae 2-10 were substantially similar to the composition of Formula One as shown in Table 2 with some modifications. Only the ingredients whose concentration are different from those of Formula One are noted below:

Formula 2: Same as Formula One except that the concentration of benzalkonium chloride was reduced 10 fold to 0.013%.

Formula 3: Same as Formula One except that betaine concentration was increased to 6% and benzalkonium chloride concentration was reduced to 0.013%.

Formula 4: Same as Formula One except that allantoin concentration increased to 1% and benzalkonium chloride reduced to 0.013%.

Formula 5: Same as Formula One except that benzalkonium concentration was reduced to 0.010%.

Formula 6: Same as Formula One except that Glycolic acid was replaced by citric acid as an alternative alpha hydroxy acid and benzalkonium chloride was reduced to 0.013%.

Formula 7: Same as Formula One except that benzalkonium chloride was replaced by grapefruit seed extract as an alternative antimicrobial substance.

Formula 8: Same as Formula One except that colloidal silver was removed and benzalkonium chloride concentration reduced to 0.013%.

Formula 9: Same as Formula One except that phenonip and colloidal silver were removed and replaced with citric acid as preservative in solution with benzalkonium chloride concentration reduced to 0.013%.

Formula 10: Same as Formula One except that Vitamin B3 and Vitamin C were added to Formula 10.

The Kill rates were measured using a method that is similar to that described in Example 2. Briefly, Methicillin resistant *staphylococcus aureus* and *Pseudomonas aeruginosa* were grown in tryptic soy broth and diluted and plated to determine the control concentrations. The bacteria were diluted 1:10 in a test substance containing one of the compositions from Formulae 2-10. The bacteria were allowed to be in contact with the test substance for 15 second contact time prior to being neutralized with Letheen broth. The bacteria were then subject to serial dilutions at a ratio of 1:10 for each dilution step before being plated in duplicate. The plates were then incubated at 37 degrees C. for 72 hours. The plates were read and the number of colonies was recorded for each plate. Logarithmic calculations were performed for log reduction calculation.

The results of these tests are shown below in Table 3.

TABLE 3

Kill Rates of Formulae 2-10

| Formula of Test Solution | Pseudomonas-Log reduction |
|---|---|
| 2 | Greater than 99.999% |
| 3 | Greater than 99.99% |
| 4 | Greater than 99.999% |
| 5 | Greater than 99.999% |
| 6 | Greater than 99.99% |
| 7 | Greater than 99.999% |
| 8 | Greater than 99.99% |
| 9 | Greater than 99.999% |
| 10 | Greater than 99.999% |

All of Formulae 2-10 showed bacterial kill rate of at least 99.99%.

Example 4

The Advanced Hand Sanitizer Composition Shows Improved Duration of Action

In order to determine the duration of action by the disclosed advanced hand sanitizer composition as compared to conventional soap and water, 32 human subjects were recruited and divided into two groups, Group I and II, with each group having 16 subjects. The hands of Group I subject were cleansed and sanitized with conventional soap and water. Group II hands were cleansed and sanitized with Formula One. Three hours after the cleansing and sanitizing, Groups I and II were each inoculated with about 585 million bacteria. The "Glove Juice Test Recovery" method was employed to determine the number of bacteria that survive the action of the sanitizer composition. See, e.g., Leyden et al., Infect Control Hosp Epidemiol. 10(10):451-4 (1989). The results are summarized in Table 4. Conventional wash and sanitization by soap and water were used as a control. The Advance hand sanitizer composition had greater than 1 log reduction of the bacteria as compared to the control.

TABLE 4

Duration of Action by the Advance hand sanitizer

|  | Control | Advanced hand sanitizer |
|---|---|---|
| Initial Inoculation | $5.85 \times 10^8$ | $5.85 \times 10^8$ |
| Post-contact recovery | $4.0 \times 10^5$ | $3.2 \times 10^4$ |

Example 5

The Advanced Hand Sanitizer Composition Shows Improved Duration of Action when Compared to Standard Hand Sanitizer Containing the Same Anti-Microbial To determine the underlying mechanisms for the higher efficacy of the Advanced hand sanitizer disclosed herein, the composition prepared in Example 1 was compared with a standard benzalkonium based hand sanitizer that contained 0.13% benzalkonium chloride, cetrimonium chloride, diglycerol, disodium cocamphodiacetate, fragrance, glycerin, hydrochloric acid, methoxy PEG/PPG-7/3, aminopropyl dimethicone, methylchloroisothiazolinone, methylisothiazolinone, tetrasodium EDTA and water, along with a control using conventional soap and water. The test was performed essentially as described in Example 3. Briefly, all subjects were inoculated with the same number of bacteria, and the numbers of bacteria that survive the treatments by the control, the standard benzalkonium based hand sanitizer, and the advanced benzalkonium based hand sanitizer (Table 2) were determined and summarized in Table 5.

TABLE 5

Higher Efficacy of the Advanced hand sanitizing composition

|  | Control | standard benzalkonium based hand sanitizer | advanced benzalkonium based hand sanitizer |
|---|---|---|---|
| Subject 1 | $1.7 \times 10^6$ | $1.8 \times 10^5$ | $3.4 \times 10^4$ |
| Subject 2 | $2.0 \times 10^6$ | $2.0 \times 10^5$ | $1.5 \times 10^4$ |
| Subject 3 | $6.0 \times 10^5$ | $4.5 \times 10^6$ | Less than $10^3$ |
| Subject 4 | $8 \times 10^5$ | $1.6 \times 10^6$ | Less than $10^3$ |

In a separate study, a larger number of subjects were recruited and evaluated to compare the efficacy and duration of the following three compositions (collectively "study agents"):
(A) regular soap and water;
(B) Commercially available Benzalkonium Chloride based hand sanitizer; and
(C) advanced hand sanitizer of Example 1.
Briefly, each study subject underwent a warm water hand wash upon arrival. After hands were dried with paper towels, each subject underwent treatment with study agent (A), (B) or (C) according to the randomization of groups as detailed above. The subjects' hands were then covered lightly with sterile paper drape and subjects were observed for 3 hours to assure that no contamination occurred. Three hours after the randomized hand treatment was provided, 1.5 ml aliquots of concentrated *Serratia marcessans* were applied to the cupped hands of the participant and gently rubbed into the skin for 30 seconds followed by a one minute rest period. This maneuver of application and rubbing was repeated 3 times. Following an additional 2 minute waiting period, sterile gloves were applied to both hands by research personnel.

60 ml of recovery fluid were introduced into each glove and held within the gloves using rubber bands at the wrist. One full minute massage was then performed to both hands of the study subject by research personnel. One ml aliquots were removed and added to tubes of broth with added quaternary ammonium inactivators. Serial dilutions and agar plating were then performed. All plates were incubated for 48 hours prior to colony counting and analysis of recovered *Serratia* colonies. Serial dilutions and plating were also performed to determine the inoculated *Serratia* concentrations.

As shown in Table 6 below, the Log reduction averaged over 12 hands per group are $3.36 \times 10^3$ for (A), $2.76 \times 10^4$ for (B) and $1.59 \times 10^6$ for the presently disclosed composition (C). Previous studies have shown no significant protection using an alcohol based sanitizer beyond 15 minutes (less than log 1 reduction) using an identical *Serratia* inoculation and glove juice test model (data not shown).

TABLE 6

Reduction of pathogens by Advanced hand sanitizing composition

| Subject | Study Agent | Inoculum | CFU recovered |
|---|---|---|---|
| Subject 1-Left | A | $5.85 \times 10(8)$ | $1.2 \times 10(5)$ |
| Subject 1-Right | A | $5.85 \times 10(8)$ | $2.3 \times 10(5)$ |
| Subject 2-Left | A | $5.85 \times 10(8)$ | $4.0 \times 10(6)$ |
| Subject 2-Right | A | $5.85 \times 10(8)$ | $7.0 \times 10(5)$ |
| Subject 3-Left | C | $5.85 \times 10(8)$ | $1.4 \times 10(3)$ |
| Subject 3-Right | C | $5.85 \times 10(8)$ | $2.7 \times 10(3)$ |
| Subject 4-Left | A | $5.85 \times 10(8)$ | $1.0 \times 10(6)$ |
| Subject 4-Right | A | $5.85 \times 10(8)$ | $3.6 \times 10(7)$ |
| Subject 5-Left | C | $5.85 \times 10(8)$ | $3.3 \times 10(4)$ |
| Subject 5-Right | C | $5.85 \times 10(8)$ | $1.2 \times 10(3)$ |
| Subject 6-Left | B | $5.85 \times 10(8)$ | $5.0 \times 10(5)$ |
| Subject 6-Right | B | $5.85 \times 10(8)$ | $2.1 \times 10(5)$ |
| Subject 7-Left | B | $5.85 \times 10(8)$ | $8.0 \times 10(4)$ |
| Subject 7-Right | B | $5.85 \times 10(8)$ | $1.1 \times 10(5)$ |
| Subject 8-Left | C | $5.85 \times 10(8)$ | $2.7 \times 10(2)$ |
| Subject 8-Right | C | $5.85 \times 10(8)$ | $1.4 \times 10(3)$ |
| Subject 9-Left | C | $5.85 \times 10(8)$ | $6.0 \times 10(3)$ |
| Subject 9-Right | C | $5.85 \times 10(8)$ | $2.4 \times 10(3)$ |
| Subject 10-Left | A | $5.85 \times 10(8)$ | $8.0 \times 10(6)$ |
| Subject 10-Right | A | $5.85 \times 10(8)$ | $2.1 \times 10(7)$ |
| Subject 11-Left | B | $5.85 \times 10(8)$ | $3.6 \times 10(5)$ |
| Subject 11-Right | B | $5.85 \times 10(8)$ | $5.0 \times 10(5)$ |
| Subject 12-Left | C | $5.85 \times 10(8)$ | $4.1 \times 10(3)$ |
| Subject 12-Right | C | $5.85 \times 10(8)$ | $1.1 \times 10(4)$ |
| Subject 13-Left | C | $5.85 \times 10(8)$ | $2.1 \times 10(4)$ |
| Subject 13-Right | C | $5.85 \times 10(8)$ | $8.0 \times 10(3)$ |
| Subject 14-left | A | $5.85 \times 10(8)$ | $2.4 \times 10(6)$ |
| Subject 14-Right | A | $5.85 \times 10(8)$ | $5.0 \times 10(5)$ |
| Subject 15-Left | B | $5.85 \times 10(8)$ | $3.3 \times 10(5)$ |
| Subject 15-Right | B | $5.85 \times 10(8)$ | $1.2 \times 10(6)$ |
| Subject 16-Left | B | $5.85 \times 10(8)$ | $4.7 \times 10(4)$ |
| Subject 16-Right | B | $5.85 \times 10(8)$ | $2.5 \times 10(5)$ |
| Subject 17-Left | A | $5.85 \times 10(8)$ | $2.9 \times 10(5)$ |
| Subject 17-Right | A | $5.85 \times 10(8)$ | $4.8 \times 10(6)$ |

TABLE 6-continued

Reduction of pathogens by Advanced hand sanitizing composition

| Subject | Study Agent | Inoculum | CFU recovered |
|---|---|---|---|
| Subject 18-Left | B | $5.85 \times 10^{8}$ | $7.0 \times 10^{4}$ |
| Subject 18-Right | B | $5.85 \times 10^{8}$ | $1.5 \times 10^{5}$ |

Bioburden control three hours after use of the Advanced Hand Sanitizer as disclosed herein is significantly improved over that of soap and water or a commercially available Benzalkonium Chloride based hand sanitizer. Averaged log reduction for soap and water, Benzalkonium Chloride, and advanced Hand Sanitizer were Log 3, Log 4 and Log 6 respectively. This data obtained using an accepted Inoculum/glove juice test model on human study subjects confirmed the ability of this Advanced Hand Sanitizer to continue to provide protection significantly longer than the other two hand cleansing/sanitizer options.

Changes may be made in the above compositions and methods without departing from the scope hereof. It should thus be noted that the matter contained in the above description should be interpreted as illustrative and not in a limiting sense. The following claims are intended to cover all generic and specific features described herein, as well as all statements of the scope of the present methods and compositions, which, as a matter of language, might be said to fall therebetween.

We claim:

1. A composition suitable for skin cleansing or skin protection, said composition comprising an aqueous solution of:
   0.13% w/w benzalkonium chloride;
   0.5% w/w allantoin;
   3.0% w/w aloe;
   2.0% w/w betaine;
   0.3% w/w dimethicone;
   0.35% w/w glycolic acid;
   0.6% w/w colloidal silver;
   0.02% w/w of a chelating agent;
   0.65% w/w of a preservative;
   wherein the aqueous solution is titrated with potassium hydroxide to a pH of 6.3.

* * * * *